United States Patent [19]
Asculai et al.

[11] Patent Number: 5,972,906
[45] Date of Patent: *Oct. 26, 1999

[54] TREATMENT OF MUCOUS MEMBRANE DISEASE, TRAUMA OR CONDITION AND FOR THE RELIEF OF PAIN THEREOF

[75] Inventors: Samuel Simon Asculai; Alan Lawrence Russell; Rudolf Edgar Falk, all of Mississauga, Canada

[73] Assignee: Hyal Pharmaceutical Corporation, Mississauga, Canada

[ * ] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/503,919

[22] Filed: Jul. 19, 1995

Related U.S. Application Data

[63] Continuation-in-part of application No. 07/675,908, Jul. 3, 1991, and a continuation-in-part of application No. 07/838,674, Feb. 21, 1992, abandoned, and a continuation-in-part of application No. 07/838,675, Feb. 21, 1992, Pat. No. 5,639,738, and a continuation-in-part of application No. 08/018,754, Feb. 17, 1993, and a continuation-in-part of application No. 08/018,508, Feb. 17, 1993, Pat. No. 5,792,753, and a continuation-in-part of application No. 08/290,840, Oct. 27, 1994, and a continuation-in-part of application No. 08/290,848, Aug. 19, 1994.

[51] Int. Cl.$^6$ ..................................................... A61K 31/70
[52] U.S. Cl. .................................. 514/54; 514/23; 514/62; 536/53; 536/55.2
[58] Field of Search .................................. 514/54, 23, 62; 536/55.2, 53; 543/562

[56] References Cited

U.S. PATENT DOCUMENTS

| | | | |
|---|---|---|---|
| 5,442,053 | 8/1995 | della Valle et al. | 536/55.1 |
| 5,514,667 | 5/1996 | Cullis-Hill | 514/54 |

*Primary Examiner*—Elli Peselev
*Attorney, Agent, or Firm*—Ivor M. Hughes; Neil H. Hughes; Marcelo K. Sarkis

[57] ABSTRACT

A method for the treatment of mucous membrane trauma disease or condition for the relief of pain associated therewith comprising administering topically an effective amount of a composition comprising an N.S.A.I.D. and a form of hyaluronic acid selected from hyaluronic acid, pharmaceutically acceptable salts thereof, fragments thereof and/or subunits thereof.

13 Claims, 14 Drawing Sheets

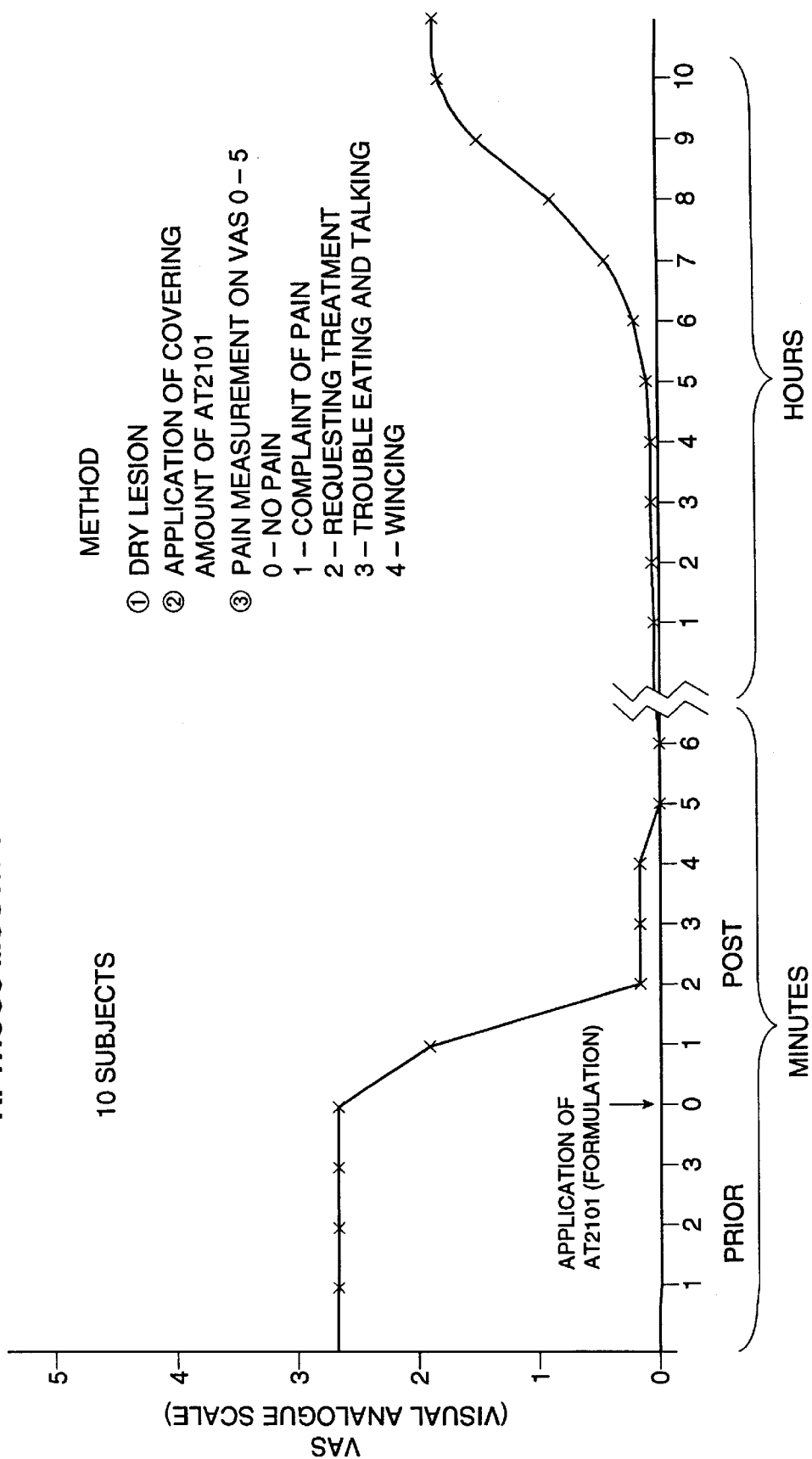

APTHOUS MOUTH ULCERS - RESPONSE TO POWDERD AND LOCALLY APPLIED ASPIRIN
EFFECT OF MOUTHWASH

FIGURE 4A

TREATMENT OF MUCOUS MEMBRANE DISEASE, TRAUMA OR CONDITION AND FOR THE RELIEF OF PAIN THEREOF

This Application is a Continuation-In-Part Application of U.S. patent application Ser. No. 07/675,908 filed Jul. 3, 1991; Ser. No. 07/838,674 filed Feb. 21, 1992 now abandoned; Ser. No. 07/838,675 filed Feb. 21, 1992 now U.S. Pat. No. 5,639,738; Ser. No. 08/018,754 filed Feb. 17, 1993; Ser. No. 08/018,508 filed Feb. 17, 1993; Ser. No. 08/290,840 filed Oct. 27, 1994 now U.S Pat. No. 5,792,753; and Ser. No. 08/290,848 filed Aug. 19, 1994 each of which is incorporated herein by reference.

FIELD OF INVENTION

This invention relates to the treatment of the mucosal membrane and cells of the mouth and the cells lining the pulmonary and vaginal cavity including mucous membrane injury and disease comprising viral and traumatic mucosal injury and the pain associated therewith. In one aspect, this invention relates to the treatment of aphthous and other oral ulceration including the pain associated therewith. In another aspect, the invention relates to the treatment of abrasions of the mucosa (as for example, when one bites his/her tongue and/or the inside of his/her cheek, buccal or labial mucosa). In another aspect, this invention relates to the treatment of leukoplakia and other precancerous conditions of the mouth and painful mouth disorders such as burning mouth syndrome. This invention also relates to dosage amounts of pharmaceutical compositions suitable for use in such treatments and the pharmaceutical compositions from which the dosages can be taken.

BACKGROUND OF INVENTION

Mention is made in "Recurrent Aphthous Ulceration: Diagnosis and Therapy" by R. J. Conklin et. al. in the March/April 1994 issue of Canadian Journal of Dermatology, of the use of anti-inflammatory therapy in cases of aphthous and other oral ulceration.

As is known, Benzydamine is already accepted as a symptomatic treatment for oral inflammation. Being an N.S.A.I.D., Benzydamine would also be expected to have superficial analgesic action. In fact, TANTUM™ containing Benzydamine is widely known and is accepted as a symptomatic treatment for oral and specifically, tonsillar inflammation with purported superficial analgesic action. However, the action of this drug and other known regimens of treatment are not fast enough and are not, in other respects, entirely satisfactory. For example, while Benzydamine has been available as a local treatment for real pain, it suffers many disadvantages in its format being an untargeted native N.S.A.I.D. Despite the disadvantages, Benzydamine has gained a worldwide use as a topical oral anti-inflammatory agent.

Tetracycline oral suspension has also been used. However, the treatment has side effects and is usually ineffective.

Applicants are also aware of the product Kenalog in Orabase. Kenalog is the trademark of E. R. Squibb for the steroid triaincinolone acetonide. Triaincinolone Acetonide is a steroidal anti-inflammatory agent. Orabase base acts as a vehicle for the triaimcinolone acetonide and sealant. This product has been used in the management of painful mucosal lesions in the mouth. However, the preparation does not have a fast analgesic action. Nor is the use of a steroid desirable. Particularly, use of a steroid reduces the body's response to infection and although widely used scientifically, it is contra-indicated to use a steroid in the presence of a viral or bacterial infection.

It is therefore, an object of the invention to provide improved treatment for mucous membrane injury and disease including viral and traumatic mucosal injury.

It is further an object of the invention to provide an improved treatment of aphthous and other oral ulceration.

It is still a further object of this invention to provide an improved treatment of leukoplakia and other conditions of the mouth.

It is a further object of this invention to provide an improved treatment for the oral, pulmonary and vaginal cavities injured by disease or injury and the pain associated therewith.

It is still a further object of this invention to provide pharmaceutical compositions and dosage amounts of the pharmaceutical compositions suitable for use with such treatments.

Further and other objects of the invention will be realized by those skilled in the art from the following summary of invention and detailed description of embodiments thereof.

SUMMARY OF INVENTION

Applicants have now discovered that the pain of mucous membrane injury for example, an aphthous ulcer (which is small in area e.g. about 3 sq. mm.) will be immediately relieved by applying topically to the aphthous ulcer injury at least about 15 to 25 mg. of a formulation comprising a form of a hyaluronic acid (for example, sodium hyaluronate having a molecular weight less than 750,000 daltons) together with a non-steroidal anti-inflammatory drug or agent (N.S.A.I.D.) (for example, Diclofenac sodium) wherein the amount of the forms of the hyaluronic acid is about 2.5% by weight of the formulation and the amount of Diclofenac sodium is 3% by weight of the formulation. Thus, the amount of hyaluronic acid applied is at least about 0.025×(15–25 mg) or at least about (0.375 mg–0.625 mg) of for example, sodium hyaluronate together with at least about (0.45 mg–0.75 mg) of Diclofenac sodium or equivalent amount of another N.S.A.I.D. Application of a dosage amount of as little as these amounts to the mucous membrane injury (to each aphthous ulcer) provides an immediate analgesic action within one to two minutes of the application. (The maximum amount applicable to each aphthous ulcer will be an amount which covers the aphthous ulcers and starts to drip off. This amount will depend on the consistency of the gel formulation and amount of form of hyaluronic acid (HA) and N.S.A.I.D. (non-steroidal anti-inflammatory drug or agent) in the gel formulation. )

Applicants believe the analgesic action is brought about by the initial coating of the mucous membrane followed by penetration of the injury by for example, sodium hyaluronate transporting the N.S.A.I.D. Preferably, the site of the aphthous ulcer or injury has been dried for example, by patting with gauze or cotton batting to remove/absorb saliva or other wetness before application of the dosage amount. While a single application will provide an immediate analgesic effect (in 60 seconds), more than one application may be made until the mucous membrane injury or disease no longer requires treatment. An application usually lasts at least 4–6 hours and in some cases 6–10 hours, relieving pain.

Therefore, according to one aspect of the invention, a novel method for the treatment of mucous membrane injury or disease and the pain associated therewith is provided, the method of treatment comprising applying a dosage amount of a pharmaceutical composition to the injury (for example, bite on the inside of the cheek or the tongue), or disease or condition (for example, aphthous ulcer) said composition comprising hyaluronic acid, pharmaceutically acceptable salts thereof, fragments thereof and/or subunits of these (HA) and an N.S.A.I.D., said amount of HA in the dosage amount comprising for example, at least about 0.375–0.625 mg. of the HA for each aphthous ulcer (about 3 sq. mm.) and said N.S.A.I.D. comprising at least about 0.45–0.75 mg. of N.S.A.I.D. where the N.S.A.I.D. is Diclofenac sodium, or an equivalent amount of another N.S.A.I.D. The HA preferably has a molecular weight less than 750,000 daltons. The area of injury is preferably dried before application.

According to another aspect of the invention, a dosage amount of a pharmaceutical composition is provided, the dosage amount being in a form for topical application to the mucosa and comprising:

(i) an effective non-toxic dosage amount of hyaluronic acid, a pharmaceutically acceptable salt thereof (for example, sodium hyaluronate having a molecular weight less than 750,000 daltons), fragments thereof and/or sub-units thereof and combinations thereof (for example, a dosage amount in the order of about 0.375–0.625 mg. per dosage application or more), and (ii) an effective non-toxic dosage amount of a non-steroidal anti inflammatory drug (N.S.A.I.D.) for example, diclofenac sodium in an amount in each dosage amount of at least about 0.45–0.75 mg. or more of said N.S.A.I.D. where said N.S.A.I.D. is Diclofenac sodium, or an equivalent amount of another N.S.A.I.D.

According to another aspect of the invention, pharmaceutical compositions are provided from which the above dosage amount can be taken and used the composition comprising suitable excipients for application to the mucosa, an N.S.A.I.D. and a form of hyaluronic acid selected from hyaluronic acid, a pharmaceutically acceptable salt thereof, fragments thereof and/or subunits thereof and combinations thereof (HA), the ratio of the HA to the N.S.A.I.D. in the composition being in the order of about $$\frac{5}{6}$$

or 0.833 and wherein the composition provides a plurality of dosage amounts described above and from which at least one dosage amount discussed above can be taken for use.

Thus, the combination covers the bite on the tongue or bite in the cheek or aphthous ulcer lesions (a dosage amount for each aphthous ulcer or bite) and soothes the nerve endings when penetration is achieved immediately reducing pain at the same time coating the nerve endings thereby insulating the nerve endings, reducing excitation of the nerve endings, desensitizing them. The combination also assists in healing each ulcer. The ulcer for example, usually clears in a week. The user usually forgets he/she even has it.

The analgesic response is extremely fast for example, within 1–2 minutes with the duration of one application extending up to 6–10 hours. We believe the hyaluronan (hyaluronic acid) molecule attaches to the ICAM-1 receptor and produces a particularly focused finding. This is important because Applicants have discovered that after the onset of analgesia, mouth rinses do not remove the medication and the analgesia remains immune to saliva and food. (This is contrasted with the effects of the use of only aspirin where after a mouth rinse (or drink) or eating, the aspirin is removed from the site of action due to failure of attachment and the analgesia disappears.

Thus, according to another aspect of the invention, Applicants have also provided an effective amount of the combination of the hyaluronic acid and/or pharmaceutically acceptable salts thereof and/or fragments and/or subunits thereof together with an N.S.A.I.D. (for example, Diclofenac sodium) for the immediate relief of the pain of aphthous ulcers and bites of the cheek for example, and the treatment thereof.

Thus, according to another aspect of the invention, Applicants have also provided the use of hyaluronic acid and/or pharmaceutically acceptable salts thereof and/or fragments thereof and/or subunits thereof together with an N.S.A.I.D. (for example, Diclofenac sodium) for the manufacture of a pharmaceutical composition from which dosage amounts of the composition for example, 15–25 mg. of the composition (2½% by weight of the form of hyaluronic acid and 3% by weight of the N.S.A.I.D. (for example, Diclofenac sodium) by weight) for the treatment of aphthous ulcers and bites of the cheek and tongue and the immediate relief of pain.

Leukoplakia is by far the most common examples of premalignancy representing 85% of such lesions. It is also the most chronic lesion of the oral mucosa, affecting 3% of white adults over 35 years having malignant transformation rates varying from 3% to 28%.

Leukoplakia's varied clinical appearance is based largely on its origin or natural progression. It is one of the few diseases in which long duration is not evidence of harmless future behaviour. Lesions of long duration actually have a greater risk of malignant transformation. Carcinomas arising from leukoplakia occur, on the average, 2½ years after the onset of the white plaque.

Leukoplakia lesions begin as thin gray or gray/white, sometimes translucent, sometimes fissured or wrinkled, and always soft and flat plaques. They are usually sharply demarcated from surrounding normal mucosa. This stage is sometimes referred to as "preleukoplakia", but it is preferably designated "thin leukoplakia."

The plaques eventually extend laterally and acquire a keratin layer thick enough to look distinctly white. They may become leathery and fissures may deepen, but there are no localized elevations above the surface plane. Most lesions remain indefinitely at this homogeneous or "thick, smooth leukoplakia" stage, but some regress or disappear and a few become more "severe".

The cause of leukoplakia remains unknown. Tobacco smoking is the most accepted factor, although obvious smoke-related keratotic changes such as nicotine platatinus are legitimately excluded from the diagnosis.

Conservative surgical excision has remained the preferred treatment for leukoplakia, although electrocautery, cryosurgery and laser ablation have also appeared effective.

Treatment sites remaining disease-free for three years need no longer be followed. Early carcinomas are typically painless but can be detected by an increased firmness, unexplained hemorrhage, chronic ulcerations, mass formation or radiographic evidence of underlying bone destruction.

According to another aspect of the invention, a novel method for the treatment of pain emanating from mucous membrane disease or injury is provided, the method of treatment comprising applying a dosage amount of a pharmaceutical composition to the injury or disease or condition, said dosage amount of the composition comprising hyaluronic acid, pharmaceutically acceptable salts thereof, fragments thereof and/or subunits and an N.S.A.I.D., said amount of the form of hyaluronic acid in the dosage amount comprising at least about 0.375–0.675 mg. and said N.S.A.I.D. comprising at least about 0.45–0.75 mg. of N.S.A.I.D., where for example, the N.S.A.I.D. is Diclofenac sodium, or an equivalent amount of another N.S.A.I.D. in for example, a composition in which the form of hyaluronic acid is 2½% by weight of the composition and 3% by weight of the N.S.A.I.D. The HA preferably has a molecular weight less than 750,000 daltons.

According to another aspect of the invention, a novel treatment of leukoplakia, (oral) mucositis, burning mouth syndrome, lichen planus, denture sores, gingivitus, recent oral surgical sites, cervical dysplasia, vulva leukoplakia and other vulval lesions, Bechets Syndrome, radiotherapy induced mucositis, post-operative gum pain, traumatic mouth lesions, post-radiotherapy vaginitis, non-specific vaginal inflammatory conditions, and other viral auto-immune and inflammatory ulcerations of the oral and vaginal mucosa is provided, said treatment comprising applying over a period of time to clear the above conditions and/or pain associated therewith, dosage amounts of a pharmaceutical composition described herein to the conditions at regular intervals (for example, every 6–8 hours) each dosage amount comprising hyaluronic acid, pharmaceutically acceptable salts thereof, fragments thereof and/or subunits, and an N.S.A.I.D., said amount of the form of hyaluronic acid in the dosage amount for each site comprising at least about 0.375–0.675 mg. and said N.S.A.I.D. comprising at least about 0.45–0.75 mg. of N.S.A.I.D. where for example, the N.S.A.I.D. is Diclofenac sodium or an equivalent amount of another N.S.A.I.D. in for example, a composition in which the form of hyaluronic acid is 2½% by weight of the composition and 3% by weight of the N.S.A.I.D. Preferably, each of the areas to which the dosage is to be applied is dried (as by patting by gauze or cotton batting).

One of the formulations which we have employed successfully in the treatments is a gel formulation comprising 3% diclofenac and 2.5% sodium hyaluronate by weight.

FORMULATION (also identified herein as AT2101 and HA.D.)

3% Diclofenac in 2.5% HA Gel

| Formula | Supplier | LOT | Amount | Percent |
| --- | --- | --- | --- | --- |
| Sterile Water | Baxter | AW456K | 1200 ml | — |
| Methoxypolyethylene Glycol 350 | Sigma | 34F-0266 | 300G (273 ml) | 20% |
| Benzyl Alcohol | BDH | 23797 | 15G (14 ml) | 1% |
| Diclofenac Sodium | Prosintex | 9123013 | 45 g | 3% |
| Sodium Hyaluronate MW 679,000 | Skymart | HG 1004 | 37.5 g | 2.5% |

Procedure

Set up stirring apparatus using a 2 liter stainless steel beaker,

Add water, Methoxypolyethylene Glycol 350, and Benzyl Alcohol and stir for 20 minutes to mix, Add Diclofenac Sodium and stir for 30 minutes to dissolve, Add Hyularonate Sodium slowly and stir initially at a high speed, but avoid splashing, After addition, stir at a slower speed for 90 minutes, the slower speed reduces the formation of air bubbles, The result is a clear transparent, viscous gel which is poured into jars and tubes. Once again, instructions accompany the container and where applicable appropriate devices for providing a premeasured amount of the composition accompany the container.

One form of hyaluronic acid and/or pharmaceutically acceptable salts thereof (for example, sodium salt) and fragments, and sub-units of hyaluronic acid, preferably hyaluronic acid and pharmaceutically acceptable salts thereof, suitable for use with Applicant's invention is a fraction supplied by Hyal Pharmaceuticals Limited. One such fraction is a 15 ml vial of Sodium hyaluronate 20 mg/ml (300 mg/vial—Lot 2F3). The sodium hyaluronate amount is a 2% solution with a mean average molecular weight of about 225,000. The fraction also contains water q.s. which is triple distilled and sterile in accordance with the U.S.P. for injection formulations. The vials of hyaluronic acid and/or pharmaceutically acceptable salts thereof may be carried in a Type 1 borosilicate glass vial closed by a butyl stopper which does not react with the contents of the vial.

The fraction of hyaluronic acid and/or pharmaceutically acceptable salts thereof (for example, sodium salt) fragments, and sub-units of hyaluronic acid, preferably hyaluronic acid and salts thereof, may comprise hyaluronic acid and/or pharmaceutically acceptable salts thereof having the following characteristics:

a purified, substantially pyrogen-free fraction of hyaluronic acid obtained from a natural source having the characteristics of subparagraphs (i) and (xii) of the following characteristics and at least one characteristic selected from the remaining characteristics of the group set out below (and preferably all characteristics) consisting of the following:

i) a molecular weight within the range of 150,000–225,000;

ii) less than about 1.25% sulphated mucopolysaccharides on a total weight basis;

iii) less than about 0.6% protein on a total weight basis;

iv) less than about 150 ppm iron on a total weight basis;

v) less than about 15 ppm lead on a total weight basis;

vi) less than 0.0025% glucosamine;

vii) less than 0.025% glucuronic acid;

viii) less than 0.025% N-acetylglucosamine;

ix) less than 0.0025% amino acids;

x) a UV extinction coefficient at 257 nm of less than about 0.275;

xi) a UV extinction coefficient at 280 nm of less than about 0.25;

and xii) a pH within the range of 7.3–7.9.

Preferably, the hyaluronic acid is mixed with water and the fraction of hyaluronic acid has a mean average molecular weight within the range of 150,000–225,000. More preferably, the fraction of hyaluronic acid comprises characteristics of sub-paragraph (xii) and at least one characteristic selected from the remainder of the group (and preferably all characteristics) consisting of the following characteristics:

i) less than about 1% sulphated mucopolysaccharides on a total weight basis;

ii) less than about 0.4% protein on a total weight basis;

iii) less than about 100 ppm iron on a total weight basis;

iv) less than about 10 ppm lead on a total weight basis;

v) less than 0.00166% glucosamine;

vi) less than 0.0166% glucuronic acid;

vii) less than 0.0166% N-acetylglucosamine;

viii) less than 0.00166% amino acids;

ix) a UV extinction coefficient at 257 nm of less than about 0.23;

x) a UV extinction coefficient at 280 nm of less than 0.19;

and xii) a pH within the range of 7.5–7.7.

Applicants also propose to use sodium hyaluronate produced and supplied by LifeCore™ Biomedical, Inc., having the following specifications:

| Characteristics | Specification |
| --- | --- |
| Appearance | White to cream colored particles |
| Odor | No perceptible odor |
| Viscosity Average Molecular Weight | <750,000 Daltons |
| UV/Vis Scan, 190–820 nm | Matches reference scan |
| OD, 260 nm | <0.25 OD units |
| Hyaluronidase Sensitivity | Positive response |
| IR Scan | Matches reference |
| pH, 10 mg/g solution | 6.2–7.8 |
| Water | 8% |
| Protein | <0.3 mcg/mg NaHy |
| Acetate | <10.0 mcg/mg NaHy |
| Heavy Metals, maximum ppm | |
| As Cd Cr Co   Cu    Fe   Pb    Hg    Ni | |
| 2.0 5.0 5.0 10.0 10.0 25.0 10.0 10.0 5.0 | |
| Microbial Bioburden | None observed |
| Endotoxin | <0.07 EU/mg NaHy |
| Biological Safety Testing | Passes Rabbit Ocular Toxicity Test |

Another form of sodium hyaluronate is sold under the name Hyaluronan HA-M5070 by Skymart Enterprises, Inc. having the following specifications:

Specification's Test

| | Results |
| --- | --- |
| Lot No. | HG1004 |
| pH | 6.12 |
| Condroitin Sulfate | not detected |
| Protein | 0.05% |
| Heavy Metals | Not more than 20 ppm |
| Arsenic | Not more than 2 ppm |
| Loss on Drying | 2.07% |
| Residue on Ignition | 16.69 |
| Intrinsic Viscosity | 12.75 dl/s (XW: 679,000) |
| Nitrogen | 3.14% |
| Assay | 104.1% |
| Microbiological Counts | 80/g |
| E. coli | Negative |
| Mold and Yeast | Not more than 50/g |

Other forms of hyaluronic acid and/or its salts, and homologues, derivatives, complexes, esters, fragments and sub-units of hyaluronic acid may be chosen from other suppliers for example, those described in prior art documents provided the form of hyaluronic acid chosen is suitable for the transport of the medicine. Where the medicine is of too high a molecular weight to be suitable, it may be autoclaved to a lower molecular weight for use.

The following references teach hyaluronic acid, sources thereof, and processes for the manufacture and recovery thereof which may be suitable.

U.S. Pat. No. 4,141,973 teaches hyaluronic acid fractions (including sodium salts) having:

"(a) an average molecular weight greater than about 750,000, preferably greater than about 1,200,000—that is, a limiting viscosity number greater than about 1400 cm$^3$/g., and preferably greater than about 2000 cm$^3$/g.;

(b) a protein content of less than 0.5% by weight;

(c) ultraviolet light absorbance of a 1% solution of sodium hyaluronate of less than 3.0 at 257 nanometers wavelength and less than 2.0 at 280 nanometers wavelength;

(d) a kinematic viscosity of a 1% solution of sodium hyaluronate in physiological buffer greater than about 1000 centistokes, preferably greater than 10,000 centistokes;

(e) a molar optical rotation of a 0.1–0.2% sodium hyaluronate solution in physiological buffer of less than $-11 \times 10^3$ degree—cm$^2$/mole (of disaccharide) measured at 220 nanometers;

(f) no significant cellular infiltration of the vitreous and anterior chamber, no flare in the aqueous humour, no haze or flare in the vitreous, and no pathological changes to the cornea, lens, iris, retina, and choroid of the owl monkey eye when one milliliter of a 1% solution of sodium hyaluronate dissolved in physiological buffer is implanted in the vitreous replacing approximately one-half the existing liquid vitreous, said HUA being (g) sterile and pyrogen free and (h) non-antigenic."

Canadian Letters Patent 1,205,031 (which refers to U.S. Pat. No. 4,141,973 as prior art) refers to hyaluronic acid fractions having average molecular weights of from 50,000 to 100,000; 250,000 to 350,000; and 500,000 to 730,000 and discusses processes of their manufacture.

BRIEF DESCRIPTION OF THE DRAWINGS

FIGS. 1A and 1B depict the apthous mouth ulcers response to AT2101 (Formulation).

FIGS. 4A and 4B depict the apthous mouth ulcer response to powdered and local applied aspirin—effect of mouthwash.

DETAILED DESCRIPTION OF THE INVENTION

Figure 1B:
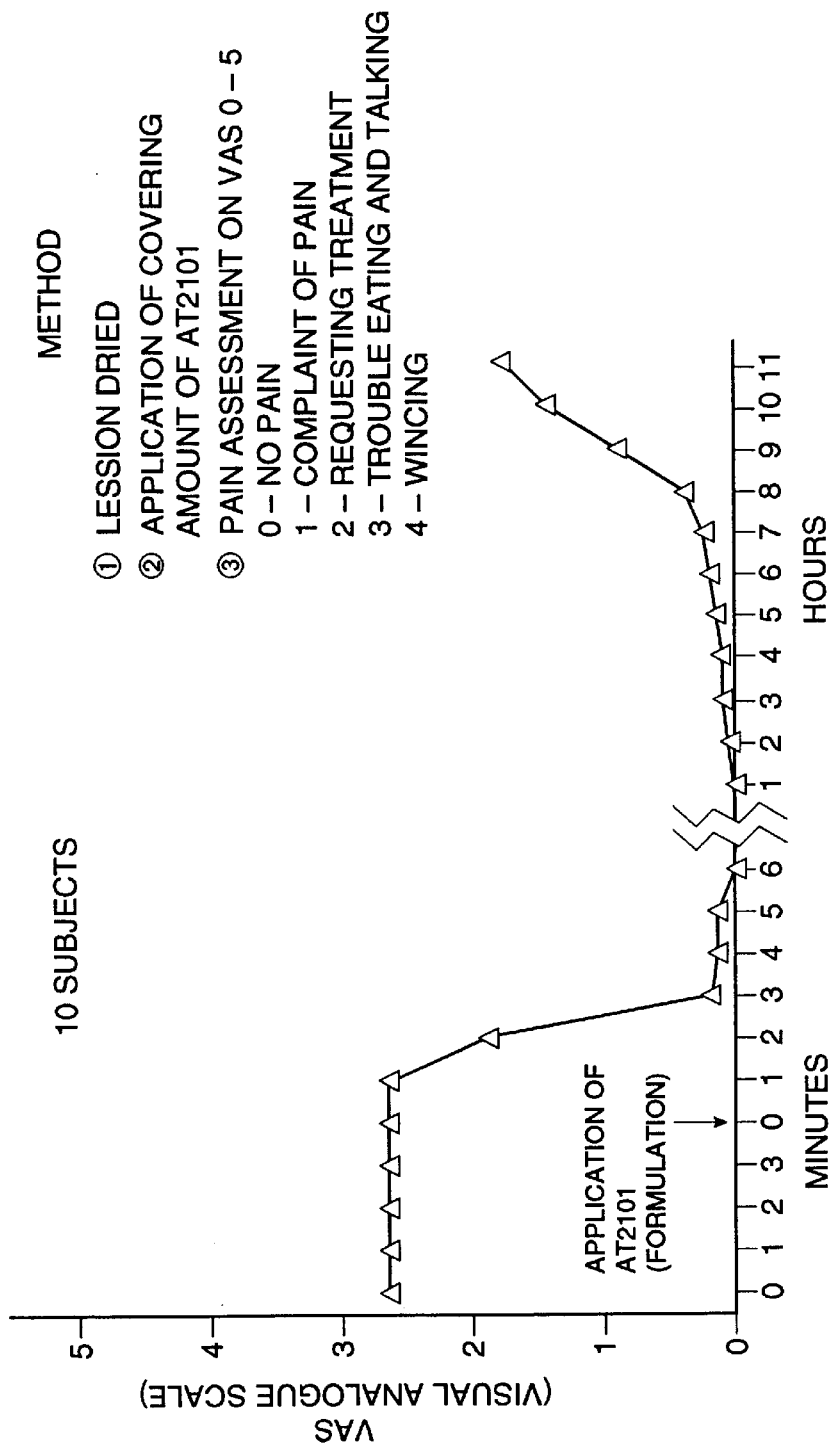

In the course of investigation of the use of the Formulation (Hyaluronan 2.5% by weight, 3% Diclofenac sodium by weight HA.D.) in the evaluation of its effect as a topical analgesic, two points emerged which needed to be differentiated. Firstly, the speed of action of HA.D. employs a direct action as an analgesic, either on free nerve endings or in blocking nociceptive chemicals, affecting free nerve endings. This has a distinct action and time from the known anti-prostaglandin action of diclofenac being a topical N.S.A.I.D. In this case hyaluronan is a carrier focusing and targeting on receptors in the lower level of the epidermis.

Our first evaluation was on small abrasions and then aphthous ulcers. We were impressed with firstly the rapid onset of analgesic response (60 seconds) and the long lasting effect in 100% of cases. This fast, 60 second response, provides a pure direct action on "nociceptive receptors", as it is far too quick for it to be an influence on an enzymatic reaction. The effect of hyaluronan alone proved ineffective (although some researchers suggest that this has a direct analgesic action on synovial membranes). We found it important before application to dry the area of ulcer, abrasion, etc., so that the HA.D. gel comes in direct contact with the "raw" or damaged mucosal area. The analgesic effect lasts many hours and we believe we are seeing in this length of duration the effect of the anti-inflammatory and perhaps even the "coating effect" of hyaluronan itself on damaged tissue and free nerve endings.

The above is the first description of the fast analgesic action of the above carrier system, providing a three-phase response. Firstly, a fast (immediate) analgesic diclofenac analgesic action, a secondary anti-inflammatory typical N.S.A.I.D. type action and thirdly a hyaluronan coating action of damaged tissue and inflamed nerve endings. Its targeting system has advantages over the pure, presently available, Benzydamine.

This coating by the form of hyaluronan covers each ulcer, soothing nerve endings when penetration occurs thereby reducing pain by coating and insulating nerve endings. The result is a reduction in the excitation of the nerve endings (desensitizes the nerve endings).

For 15 patients with aphthous ulcers treated, 5 were control and 10 were treated by dosage amounts according to the invention. For the 5 controls, no significant relief—hyaluronan (sodium hyaluronate) by itself did not work. For those patients treated with dosage amounts applied to each of the ulcers in accordance with the invention, the pain disappeared and after two days of treatment, (2–3 times to each ulcer each day or as required when the dosage wore off), the 10 patients did not need further treatment and healing proceeded and was assisted by the application of the dosage amount.

The rapid analgesic action achieved by the dosages was surprising (it was too fast to be a blocking of the accepted prostaglandin cascade); we therefore looked at many pain site models and looked to the oral mucosa with its thin lining, free pain nerve endings and, in the case of aphthous ulcers, its numerous local painful areas in developing our invention. We found the use of the topical diclofenac in the Formulation to produce pain relief within two minutes, not only in the aphthous ulceration but also other viral or traumatic mucosal injury.

The mean dosage is 15–25 mg. of the Formulation per application: the analgesic action occurs within one to two minutes. Pain relief was seen in aphthous ulcers, abrasions and other mucosal injuries. The dosages also assist in the healing process.

The observations have been confirmed in resolving pain by some of the researchers themselves. It is interesting that one such researcher was in a rush to give a lecture and all he had with him was the topical gel of the Formulation (at page 8 of Application) and he found relief within 60 seconds after application.

Ten subjects with aphthous mouth ulcers were treated with the Formulation (identified as AT2101 herein). The lesion was first dried, then covered with an application of the Formulation (AT2101) gel. Pain was assessed on a visual analogue scale (VAS) of 0–5, where 0=no pain, 1=complaint of pain, 2=request for treatment, 3=trouble eating and talking and 4=wincing. FIGS. 1A and 1B (which relate to the same test) show the rapid onset of analgesia induced by Formulation AT2101, and the length of time for which this persisted.

Figure 2A:
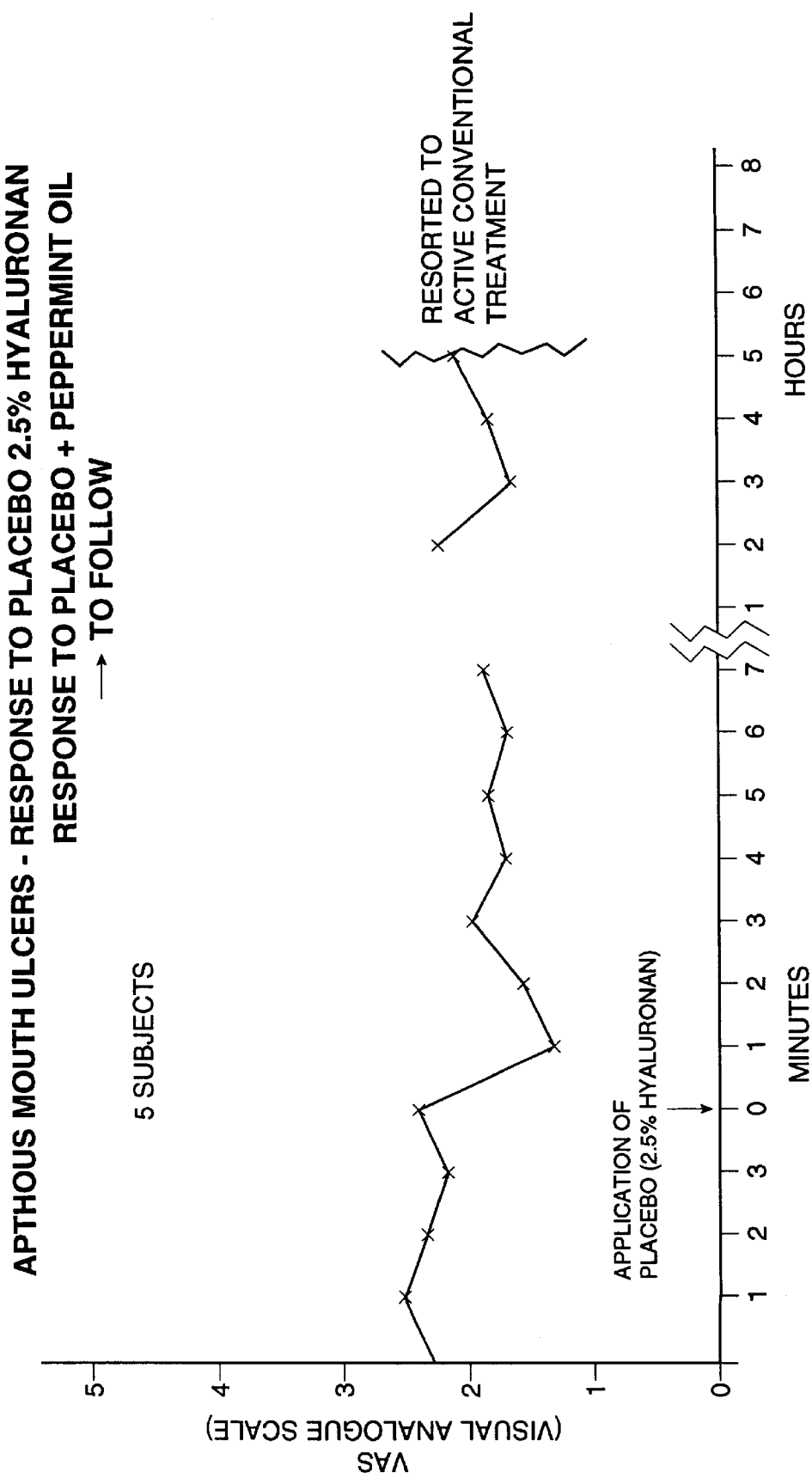
FIGS. 2A and 2B depict the apthous mouth ulcers response to placebo (2.5% hyaluronan).
Figure 2B:
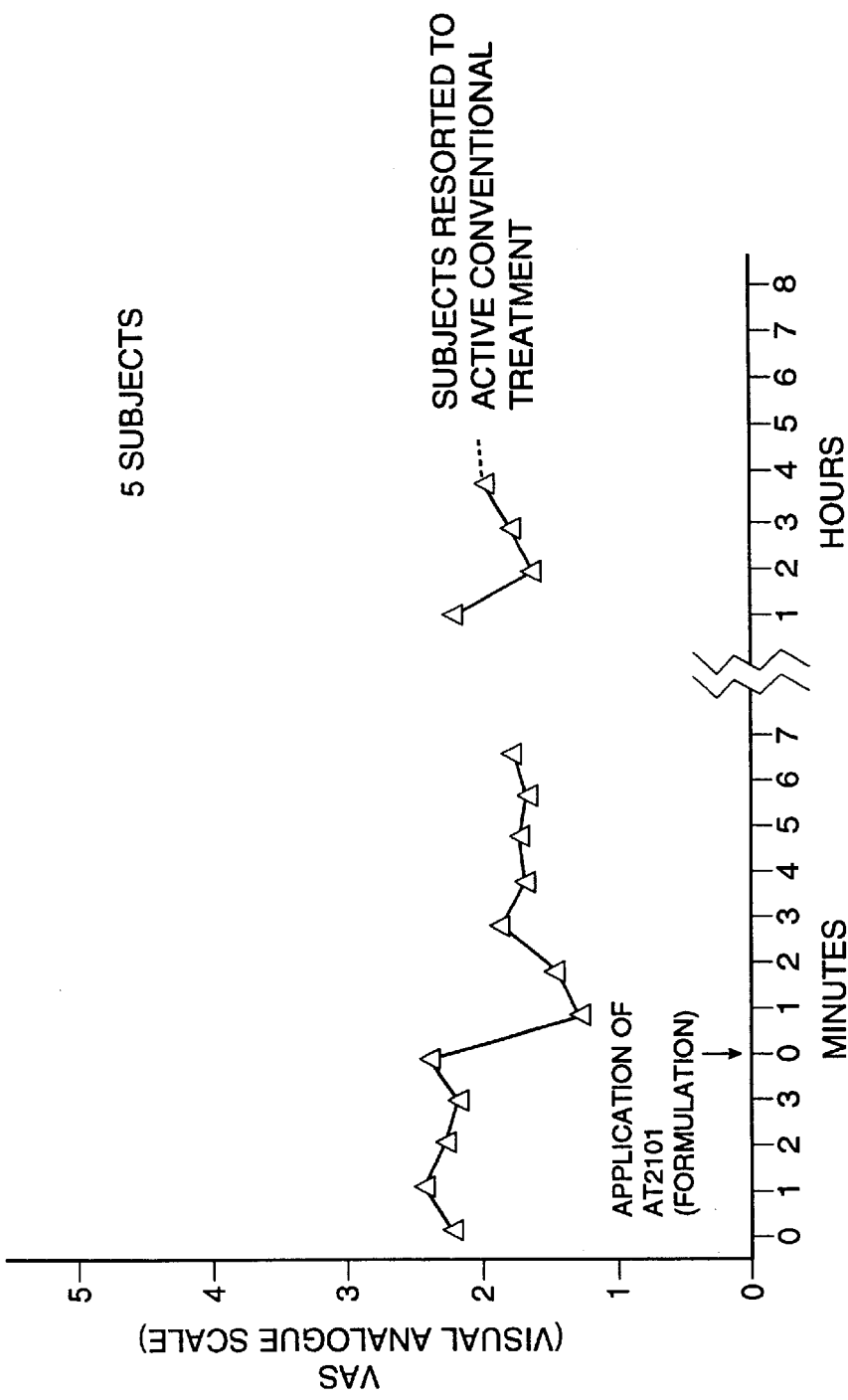

Five patients applied placebo in (2.5% by weight hyaluronan) to the mouth ulcers. A brief reduction in pain was observed following application, which appeared to have been brought about through drying the ulcer and removing the irritant mouth secretions. However, within about an hour all subjects resorted to active conventional treatment (see FIGS. 2A and 2B which are meant to depict graphically the same test).

Figure 3A:
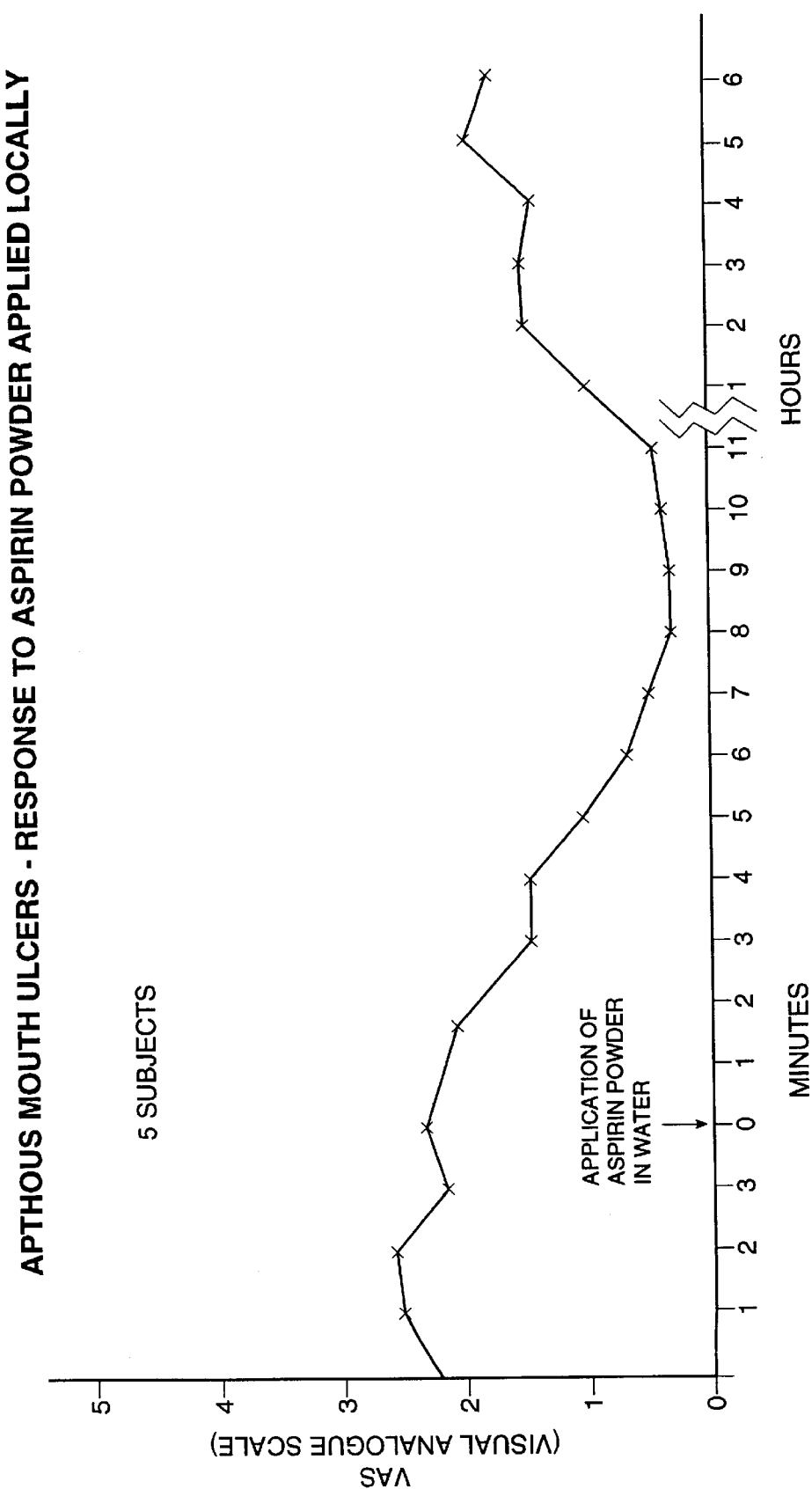
FIGS. 3A and 3B depict the apthous mouth ulcers response to aspirin powder applied locally.
Figure 3B:
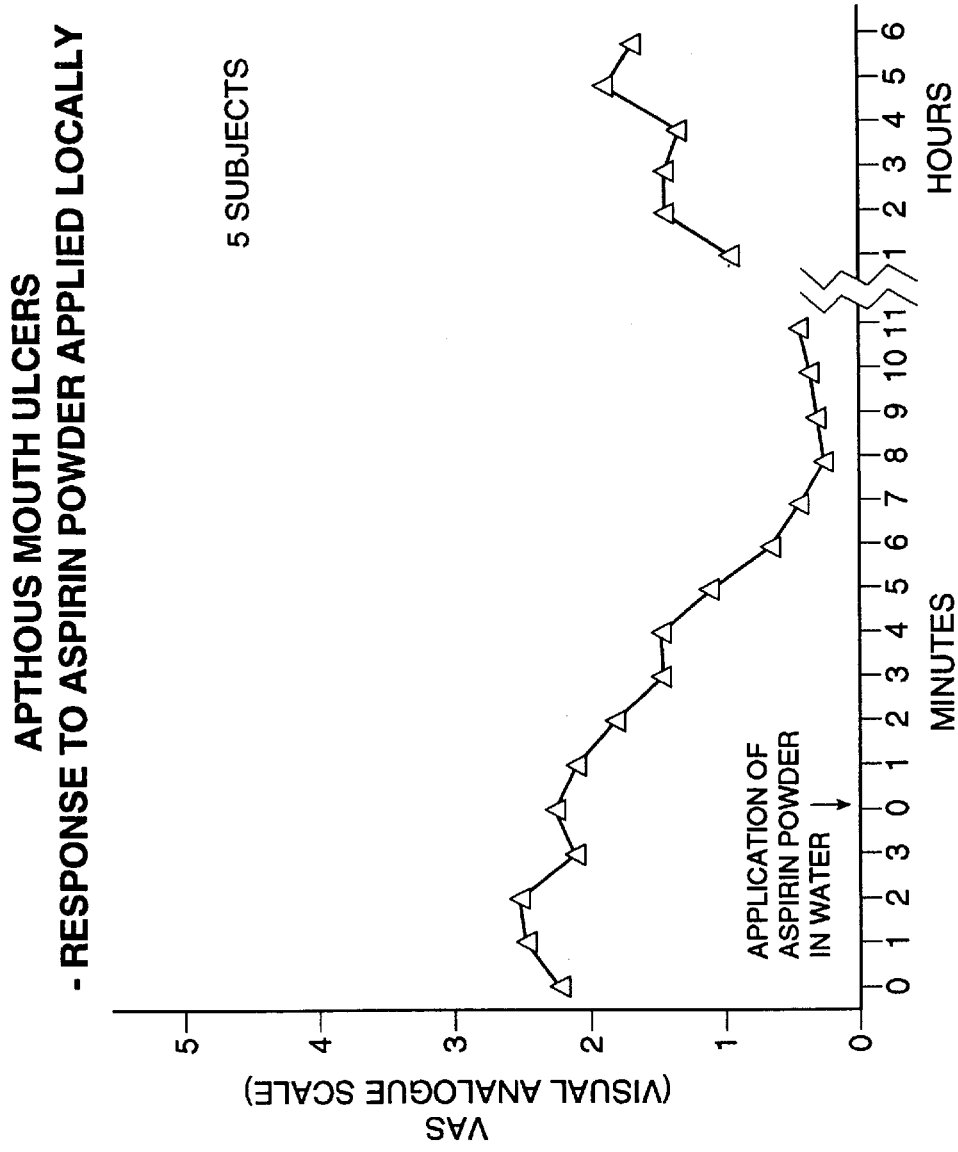

Five subjects received a 325 mg. tablet of aspirin, ground to a powder and applied in a water paste. Analgesia was slow in onset and lasted only a short time (see FIGS. 3A and 3B which are meant to illustrate graphically the same test).

Figure 4B:
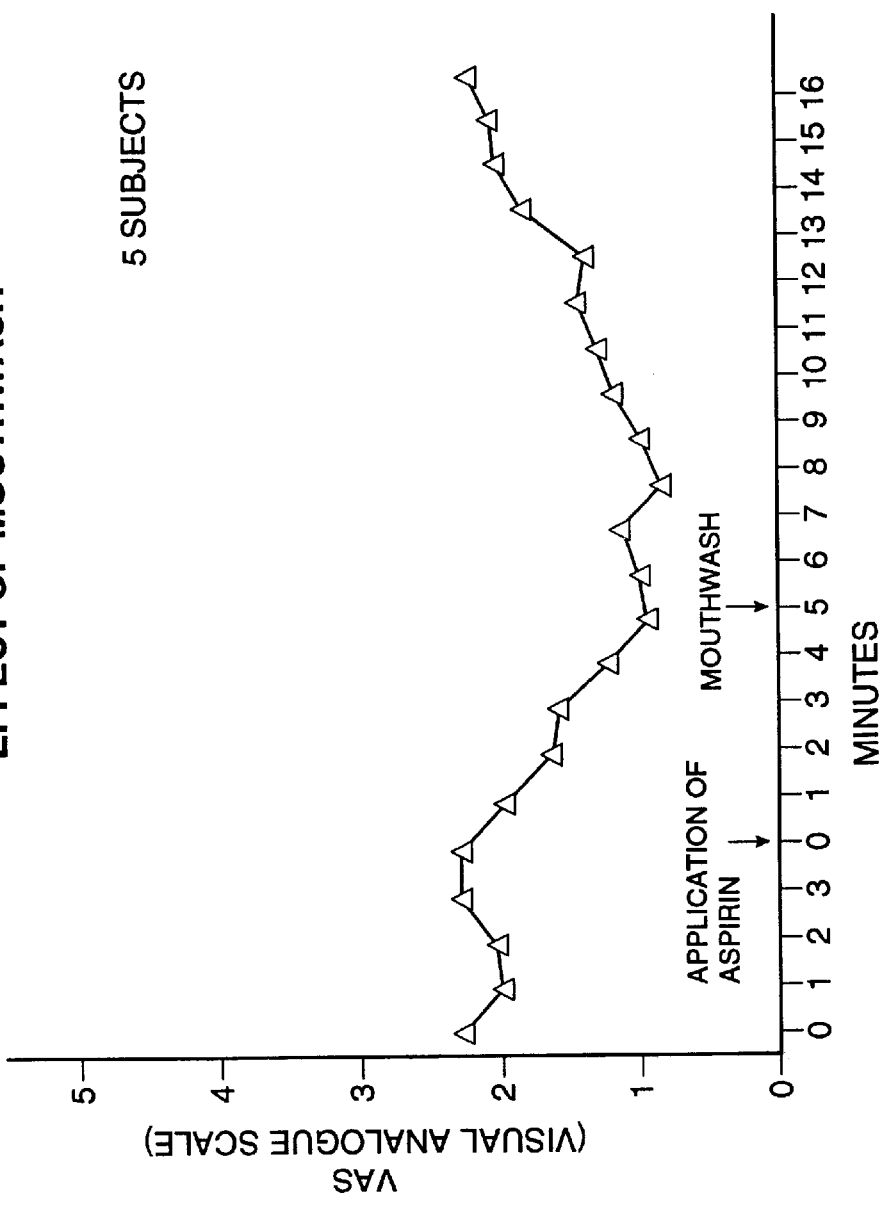
Figure 5A:
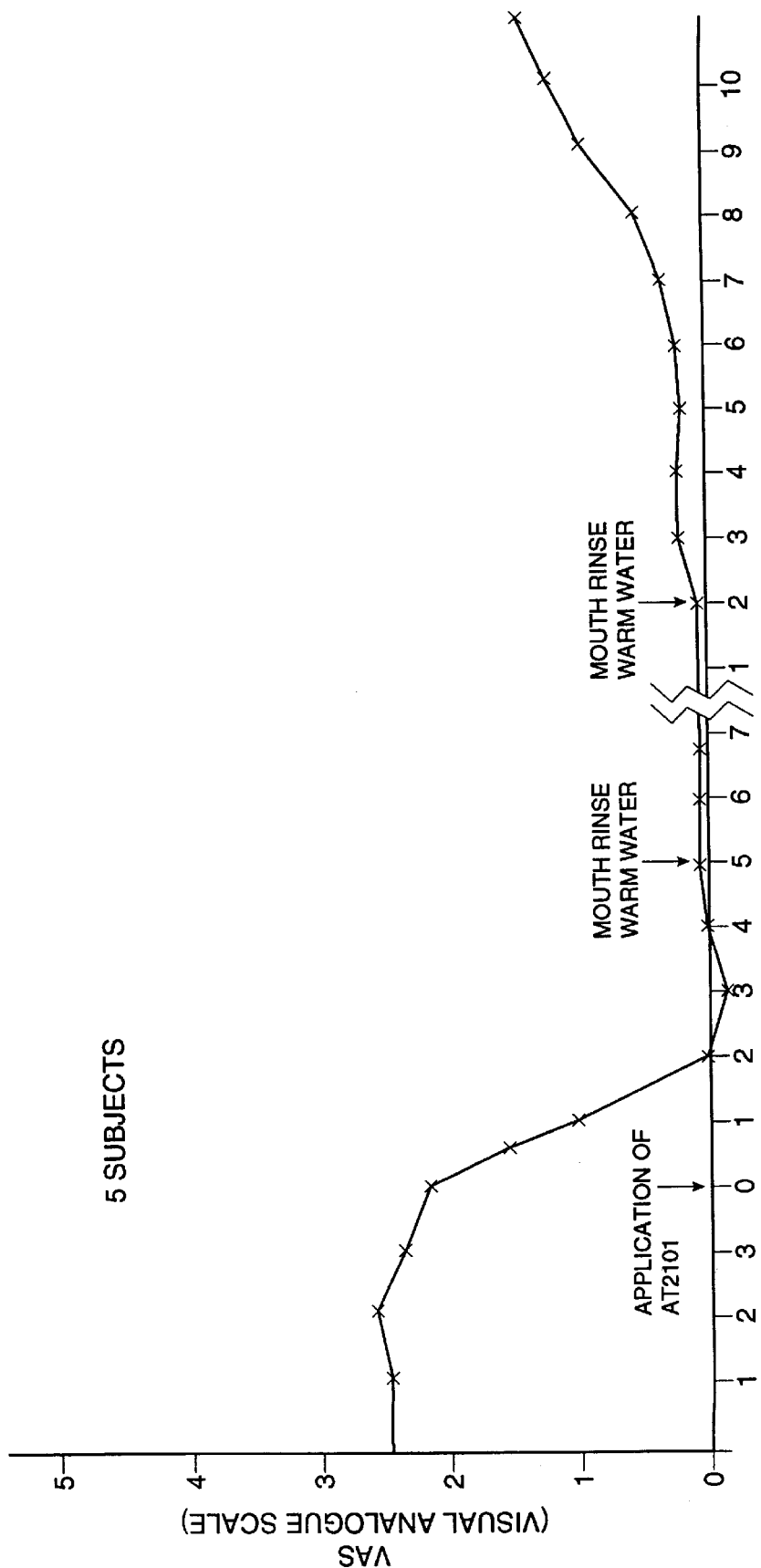
FIGS. 5A and 5B depict the apthous mouth ulcers response to AT2101—effect of mouthwash.
Figure 5B:
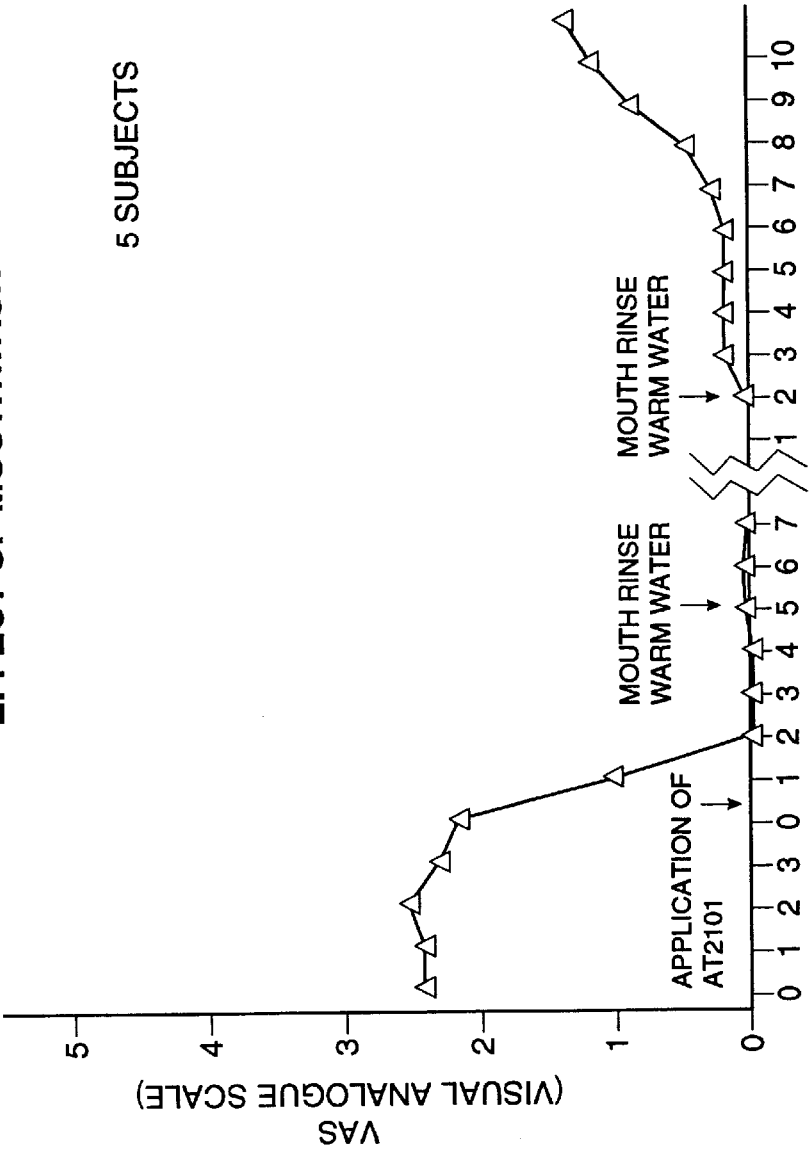

When this latter experiment was repeated, but the mouth rinsed with mouthwash five minutes after applying the aspirin paste, the analgesic effect was immediately reversed (FIGS. 4A and 4B). In contrast, however, when analgesia was induced by AT2101 Formulation and the mouth rinsed five minutes after its application, no reduction in analgesia was observed. A further rinse at 2 hours had only a slight effect on the analgesia (see FIGS. 5A and 5B which are meant to illustrate graphically the same tests).

Figure 6A:
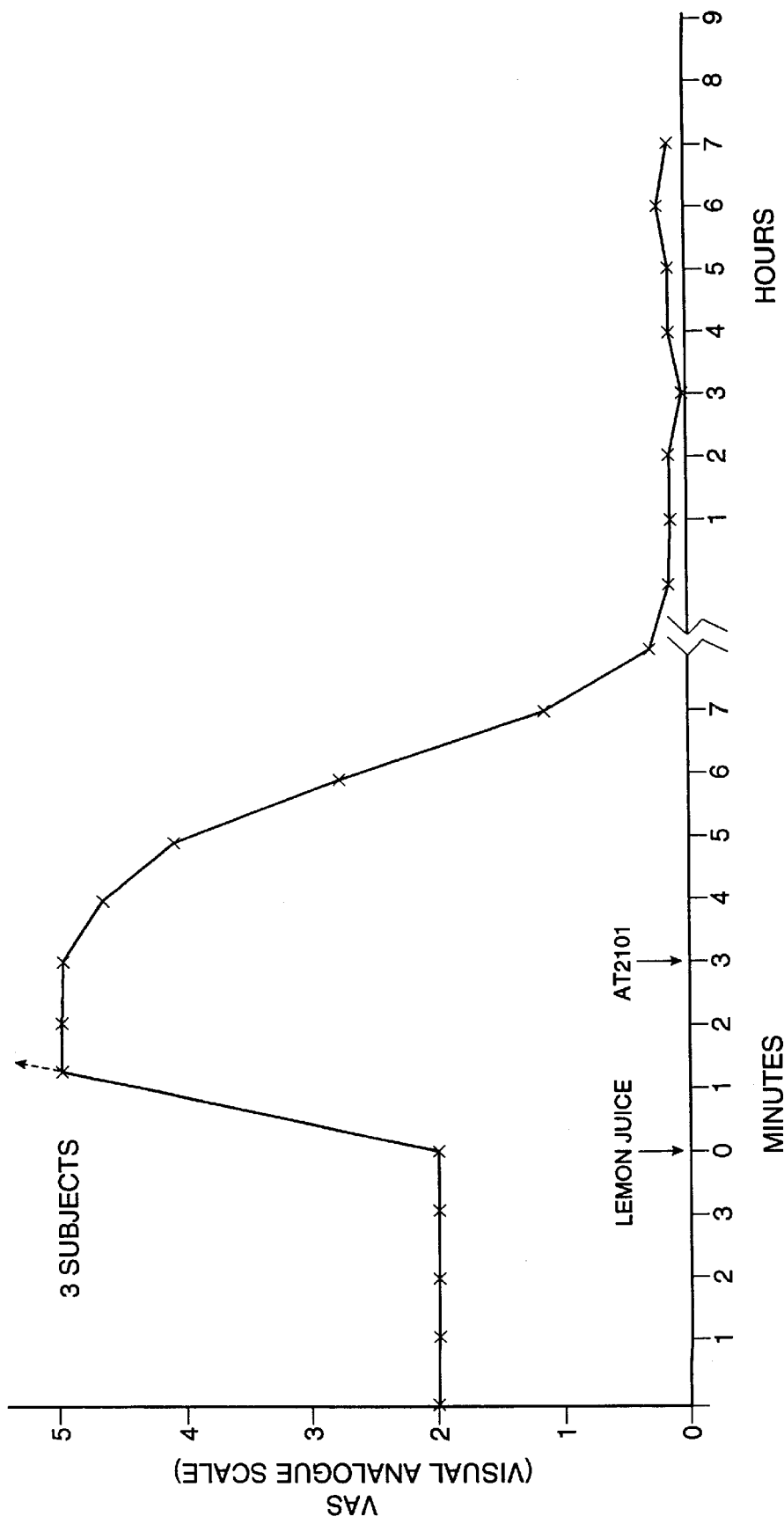
FIGS. 6A and 6B depict the apthous mouth ulcers response to citric acid to intensify pain.
Figure 6B:
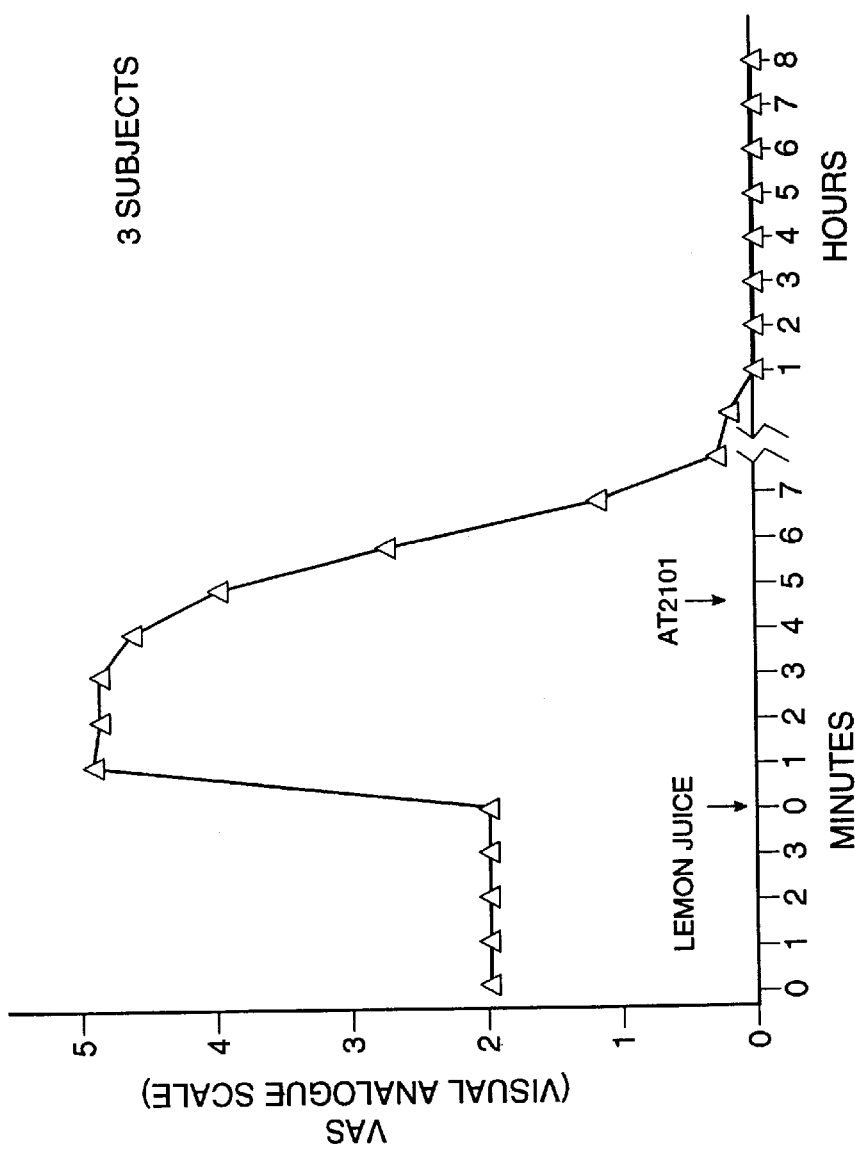
Figure 7A:
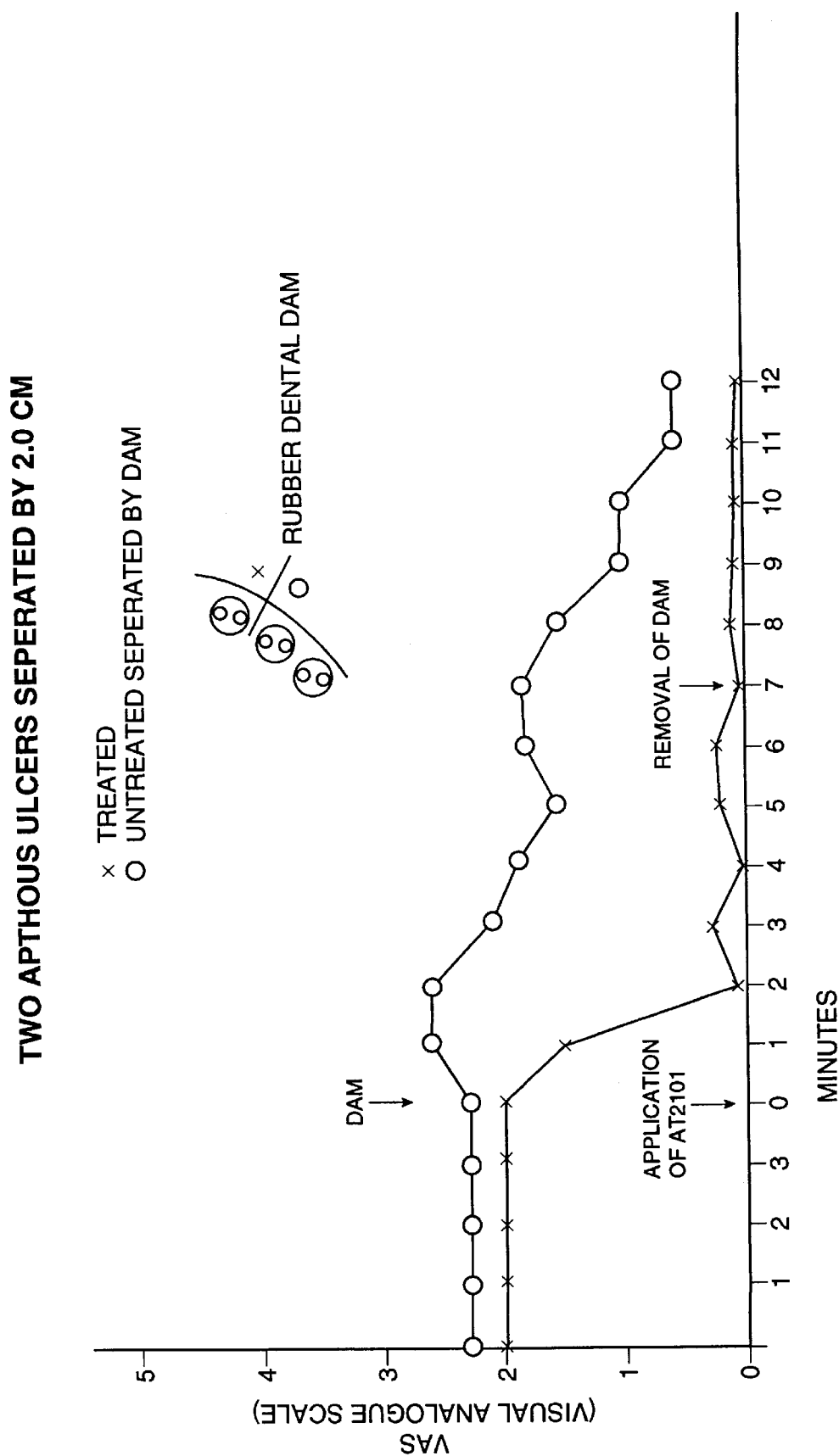
FIGS. 7A and 7B depict two apthous ulcers separated by 1.5 cm by dam, one ulcer treated, other untreated.
Figure 7B:
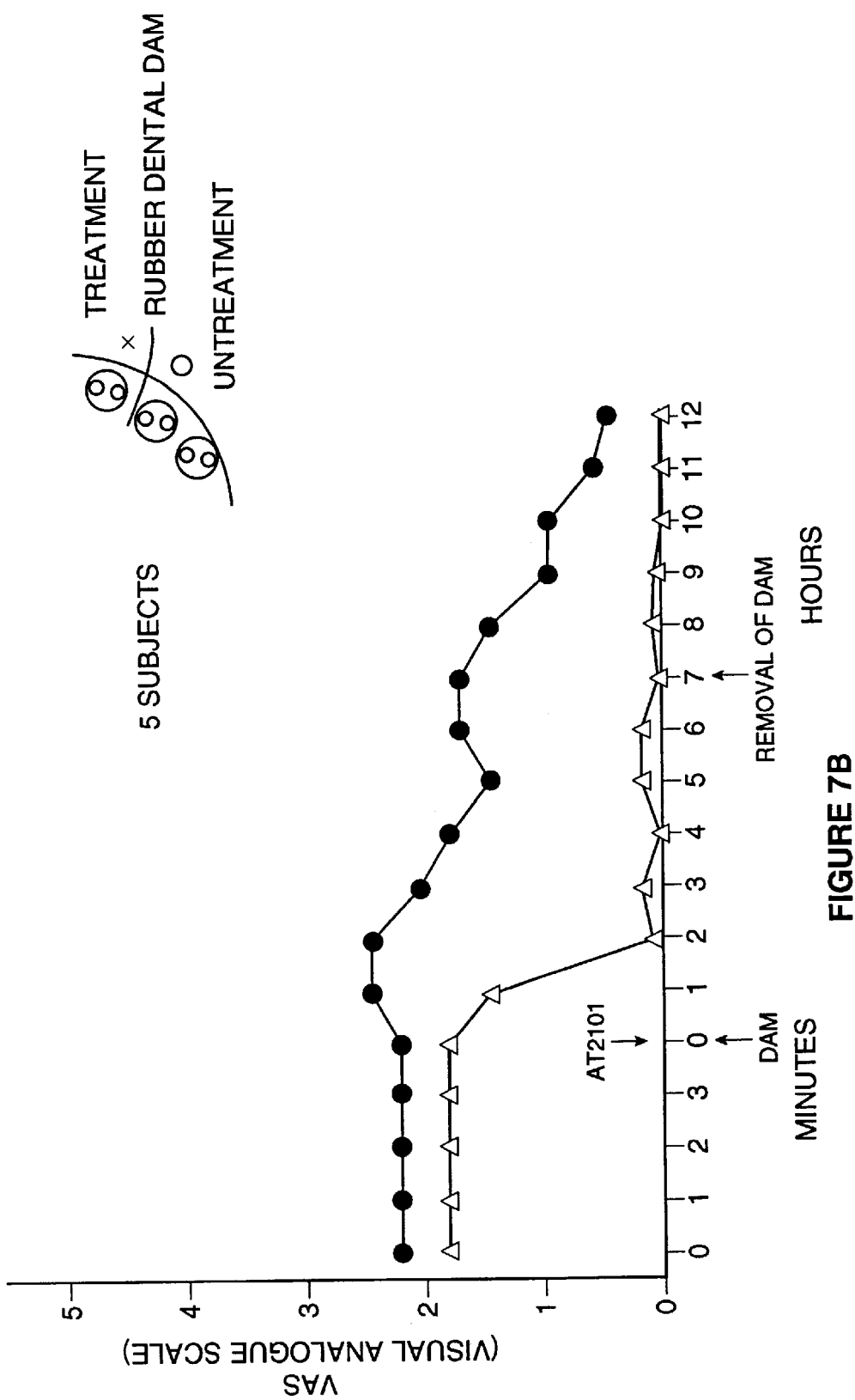

In order to assess the effect of AT2101 on more intense pain, citric acid, which induces a severe pain reaction, was placed on the mouth ulcers in three subjects, and the dosages described above from AT2101 Formulation were applied to each ulcer a few minutes later. Application of AT2101 produced complete pain relief within four minutes, an effect which lasted for several hours (see FIGS. 6A and 6B which graphically illustrate the same tests). The Placebo was ineffective. These results demonstrate that AT2101 Formulation has a rapid analgesic action and is of long duration, which is not significantly reduced by saliva, eating, or mouth rinses. Additionally, in 5 subjects who had at least two aphthous ulcers in close proximity to one another, a rubber dam was put between them to separate them. One was treated with the Formulation and the other left untreated. After about 7 minutes, the dam was removed and the pain assessed for each. Even the untreated aphthous ulcer began to feel the analgesic effect (see FIGS. 7A and 7B). The analgesic, anti-inflammatory and healing actions of this compound can also be used in the number of other oral pathologies referred to above.

Oral pain lesions are a neglected aspect of modern medicine. Mucosistis is a common complaint, often secondary to DXR and chemotherapy, adding to the distress of patients receiving treatment. Such treatment often has to be halted or scaled down due to its effect on the vulnerable and frail mucosal oral lining. Recent interest has focused on the use of capsaicin candies, in the belief that depletion of substance P will allow pain to diminish. However, this was a narrow approach, and limited by the amount of pain produced by capsaicin which seriously ill patients are unable to tolerate. The use of AT2101 for the treatment of this condition is expected to be not only a fast-acting, long-lasting analgesic, but, by destroying the prostaglandin shield, and other anti-nflammatory actions will also help the healing process. Thus, the suffering and anguish from mucositis patients with for example, cancer can be overcome. Similar results are expected with patients receiving radiation treatment in the rectal and vaginal areas.

Burning mouth syndrome is also very common, but is often shunned by physicians who have little to offer for this very disabling condition of the mouth. Here, again, AT2102 should prove to be a suitable healing agent.

Leukoplakia affects between 3% and 28% of the population and has the same histological appearance as the hypertrophic type of solar keratosis. It is expected that the use of the Formulation for leukoplakia will be successful and the pain associated therewith. Furthermore, it is expected that other dysplasias, especially cervical dysplasia will also be successfully treated (together with any pain) and the formulation and dosage amounts will be a curative agent for what is one of the most common and difficult to treat oral conditions and the increasing epidemic of cervical dysplasia. Additionally, it is expected that Intestitial cystitis can also be treated by modifying the Formulation for internal application (for example, by intravesicular administration [into the bladder]) to contain for example, sodium hyaluronate (2½% by weight) and Diclofenac sodium (3% or equivalent) by weight for treatment. The Formulation can also be modified to include glucosamine in effective amounts for intravesicular administration as an additional or other component of the Formulation.

In an attempt to evaluate the magnitude of the analgesic effect of the Formulation (also termed herein, HA.D.), in three cases, lemon juice was used on the aphthous ulcer to increase the intensity of pain to a level of wincing. The response (as shown graphically in FIGS. 6A and 6B) of HA.D. (AT2101) was just as effective in producing analgesia in a short period of time, 3 minutes, to a level that was barely discernible as painful.

The above thus clearly demonstrate the uniqueness of the Formulation (HA.D.) (AT2101) as an analgesic binding combination of uniqueness of action, combining the targeting of the hyaluronan onto the ICAM-1 receptor and the binding of Diclofenac into the molecular web.

We have therefore demonstrated:
1. Analgesic response
2. Adhesiveness of analgesic response
3. Magnitude of response
4. Local action of response (by separating aphthous ulcers using a dam, we demonstrated that only one aphthous ulcer which had the gel applied had the pain relieved whereas the other one about, a centimetre away, was still painful. When the dam or divider was released, the analgesia spread, therefore, proving it is topical.)
5. Assistance in the healing process.

An effective tool has therefore been provided in the treatment of oral pain which demonstrates a totally unique action of the topical Diclofenac in producing such a rapid analgesia. The standard theories are analgesia of N.S.A.l.D.'s is by prostaglandin inhibition or central action. However, up until now a peripheral topical rapid action, as described above, has never been previously described. The early literature describes topical aspirin as a local analgesic but it was failed to be appreciated at the time that this was a unique action and could not occur by inhibition of prostaglandins because of the time lag. Enzyme inhibition takes hours to cause changes to produce analgesia.

Our initial studies were carried out using HA.D. (the Formulation also termed AT22101) on de novo aphthous ulcers. We observed the effect on base line pain and the time of response (see FIGS. 1–7). With the idea that an irritant, such as harmless lemon juice (citric acid) would increase the intensity of the pain and allow a magnification of an analgesic effect, we started applying lemon juice to aphthous ulcers (see FIGS. 6A and 6B). As can be imagined, this produced a marked increase manyfold in the degree of pain to a degree of producing wincing or considerable discomfort. Using this as our template, we applied the gel and again observed an analgesic response over the ulcer area. This was, as expected, found in all five cases. It was interesting that on further close observation and questioning there is a slight anaesthetic action on the surrounding areas, however, this does not abort taste sensation or more importantly, awareness of the area so that there is little danger of biting one's own buccal or labial mucosa. We think this is an extremely important point which gives the gel the advantage against topical anaesthetic.

This is a unique action, being directly onto free pain fibres, since its speed of two minutes and less precludes the normally established effect of an N.S.A.I.D. by blocking prostaglandin production. There has never been such a clear cut demonstration of the pure analgesic action as in these studies with aphthous and other buccal lesions.

It is interesting to note that the lead product used today and discussed previously in the management of painful mucosal lesions in the mouth is Kenalog in Orabase. This, as previously discussed, suffers from the disadvantage that one is using a steroid which reduces the body's response to infection and although widely used scientifically it is contra-indicated to use steroid in the presence of a viral or bacterial infection.

The oral mucosa is one of the most sensitive areas for chemotherapy and often life saving treatment has to be halted because of oral pain and ulceration. HA.D. (the Formulation also AT2101) not only acts as an analgesic, the unique action being described, but by being an anti-inflammatory lowers the "prostaglandin shield" and allows the body's defences to come more into play.

Six (6) case history reports of patients that were treated with HA.D. (3% Diclofenac, 2.5% HA) gel as described below. In addition to the cases described below, the Formulation was applied to many others in respect of whom no expansive report is made herein. These patients (where no expansive written report is provided herein) were treated for denture sores, post-surgical inflammation in the mouth and traumatic ulcers in the mouth. In each case, complete analgesia was achieved within the first five minutes following application. The Formulation was also applied to buccal mucosa following topical anesthesia injections and was successful in preventing post-operative soreness and discomfort. Patients suffering from temporomandibular joint syndrome applied the gel to the skin adjacent to the joint and reported pain relief as well. A patient having lichen planus was also successfully treated—after treatment for unknown reasons, the condition recurred (see Case History Report #6 below).

Case History Report #1
Age of Patient
  52
Sex:
  F
Significant Medical History:
  Myathenia Gravis of undergoing extensive dental work.
Medications:
  Predisolone 10 mg/day
# of lesions present and sites:
  1—buccal mucosa
Size of lesion(s):
  $\geq 5$ cm diameter
Appearance of lesion(s):
  Oval flat patch covered by a white fibrinous membrane and surrounded by an erythematous halo
Presence of Pain:
  Yes
How long have lesions been present?
  1 day
Are lesions recurrent, and if so, how frequently do they present?
  No
Upon application of Hyal HA.D., what was the patient's reported response?

Initially (for first 3–5 seconds) patient reported numbness in area and subsequently analgesia.
If analgesia was achieved, how long did it last?
Duration of lesion.
Was follow-up done?
Yes
What were the results?
Resolution of lesion in 1–2 days with no scarring.
Was a second application necessary?
No.
If so, how soon after the first application was it needed?
n/a
Case History Report #2
Age of Patient:
43
Sex:
F
Significant Medical History:
Stress due to inability to eat or drink without experiencing severe oral pain.
Medications:
n/a
# of lesions present and sites:
Multiple lesions on dorsum and ventrum of tongue, buccal mucosa and palate.
Size of lesion(s):
$\geq 1$ cm diameter
Appearance of lesion(s):
Ragged areas with white/yellow fibrinous membranes surrounded by an erythematous halo.
Presence of Pain:
Yes
How long have lesions been present?
2 weeks
Are lesions recurrent, and if so, how frequently do they present?
~Every 2 weeks for 1 year; new lesions appear especially in times of stress or menses.
Upon application of Hyal HA.D., what was the patient's reported response?
Within 5 minutes, patient reported no pain and could drink water without pain.
If analgesia was achieved, how long did it last?
~6 hours
Was follow-up done?
Yes
What were the results?
Patient reported about 60% improvement of pain when gel was applied second time; then complete relief of pain when applied b.i.d.
Was a second application necessary?
Yes
If so, how soon after the first application was it needed?
~6 hours.
Case History Report #3
Age of Patient:
70
Sex:
F
Significant Medical History:
n/a
Medications:
n/a
# of lesions present and sites:
1 Buccal Vestibule
Size of lesion(s):
$\geq 1.5$ mm diameter
Appearance of lesion(s):
Flat oval patch covered by a white fibrinous membrane and surrounded by an erythematous halo.
Presence of Pain:
Yes
How long have lesions been present?
~2 days
Are lesions recurrent, and if so, how frequently do they present?
No
Upon application of Hyal HA.D., what was the patient's reported response?
Pain relief within first 5 minutes.
If analgesia was achieved, how long did it last?
Duration of lesion
Was follow-up done?
Yes
What were the results?
3 days later, patient was seen and lesion was absent.
Was a second application necessary?
No.
If so, how soon after the first application was it needed?
n/a
Case History Report #4
Age of Patient:
40
Sex:
M
Significant Medical History:
Patient smokes 1 p/p/d cigarettes; has had moderate severe periodontitis; 1 implant was placed in area of irritation~6 months ago and 2 days prior to appearance of lesion, implant abutment was uncovered with placement of 1 suture.
Medications:
n/a
# of lesions present and sites:
2—both in buccal vestibule adjacent to where dental procedure was recently performed.
Size of lesion(s):
(i) ~3 mm×2 mm; (ii) 1 cm=d
Appearance of lesion(s):
(i) Oval flat patch covered by a white, fibrinous membrane and surrounded by an erythematous halo;
(ii) Erythematous edemotous indurated area covered by a white membrane which could be rubbed off.
Presence of Pain:
Yes
How long have lesions been present?
2 days
Are lesions recurrent, and if so,how frequently do they present?
No
Upon application of Hyal HA.D., what was the patient's reported response?
For 3–4 minutes, tingling and burning; after 5 minutes, no pain whatsoever.
If analgesia was achieved, how long did it last?
Yes, 7–8 hours Was follow-up done?
  Yes
What were the results?
  Complete relief of pain reported for 7–8 hours (2nd application); 12–13 hours (3rd application). Inflammation markedly dimminished (pain, erythema, swelling).
Was a second application necessary?
  Yes
If so, how soon after the first application was it needed?
  7–8 hours later
Case History Report #5
Age of Patient:
  31
Sex:
  F
Significant Medical History:
  n/a
Medications:
  n/a
# of lesions present and sites:
  1 buccal mucosa
Size of lesion(s):
  ≧0.5 cm diameter
Appearance of lesion(s):
  Oval patch covered by a white fibrinous membrane surrounded by an erythematous halo.
Presence of Pain:
  Yes
How long have lesions been present?
  4 days
Are lesions recurrent, and if so, how frequently do they present?
  Every time patient eats something salty of chocolate.
Upon application of Hyal HA.D., what was the patient's reported response?
  First, tingling sensation; then, numbness; within~5 minutes, analgesia.
If analgesia was achieved, how long did it last?
  Yes, 2 (?)
Was follow-up done?
  No
What were the results?
  n/a
Was a second application necessary?
  n/a
If so, how soon after the first application was it needed?
  n/a
Case History Report #6
Age of Patient:
  53
Sex:
  F
Significant Medical History:
  Heart murmur.
Medications:
  Unknown.
# of lesions present and sites:
  Left-lateral border of tongue.
Size of lesion(s):
  ≧3 cm×1 cm
Appearance of lesion(s):
  White patch with irregular border that cannot be rubbed off.
Presence of Pain:
  Yes, when acidic food/drink is consumed only.
How long have lesions been present?
  Unknown
Are lesions recurrent, and if so, how frequently do they present?
  n/a
Upon application of Hyal HA.D., what was the patient's reported response?
  Tingling feeling for a few minutes.
If analgesia was achieved, how long did it last?
  Indefinitely
Was follow-up done?
  Yes
What were the results?
  Lesion appeared to resolve when gel was applied b.i.d. (twice daily).
Was a second application necessary?
  Yes
If so, how soon after the first application was it needed?
  b.id.
*Note: Patient ceased gel application for 3 days and lesion appeared worse; lesion changed shape and appeared speckled. Patient was sent for biopsy and diagnosis was lichen planus.
Further Example
  Patient suffering from aphthous ulcers of oral cavity due to overdosage of antibiotics which resulted in a change of oral flora and virus growth as well as fungal growth. Patient was debilitated and could not eat or speak; patient was in excruciating pain; patient tried both benzocaine lozenges and aspirin—neither worked.
  Patient applied dosage amounts of HA.D. gel made according to invention to areas of ulceration; patient experienced relief within 5 minutes. Pain relief lasted approximately four hours when pain returned.
  When the pain returned, dosage amounts of HA.D. gel was reapplied. Patient noted that the pain relief was not taken away by food and drink. Therefore, the patient could eat and drink without affecting analgesic effect of application of gel of dosage amount of Formulation.
  As many changes can be made to the examples without departing from the scope of the invention, it is intended that all matter be interpreted as illustrative of the invention and not in a limiting sense.

The embodiments of the invention in which an exclusive property or privilege is claimed are as follows:

1. A method for the treatment of mucous membrane trauma and the immediate relief of pain associated therewith, the method comprising administering topically an effective dosage amount of 18–25 mg of a composition comprising a non-steroidal anti-inflammatory drug (N.S.A.I.D.) and a form of hyaluronic acid selected from the group consisting of hyaluronic acid and pharmaceutically acceptable salts thereof wherein said form of hyaluronic acid has a molecular weight less than 750,000 daltons and greater than 150,000 daltons.

2. The method of claim 1 wherein the form of hyaluronic acid is sodium hyaluronate.

3. The method of claim 1 or 2 wherein the effective dosage amount of the composition contains 2½% by weight of the form of hyaluronic acid and 3% by weight of the N.S.A.I.D.

4. The method of claim 1 or 2 wherein the effective dosage amount of the composition contains 2½% by weight of the form of hyaluronic acid and 3% by weight of the N.S.A.I.D. wherein the N.S.A.I.D. is Diclofenac Sodium.

5. The method of claim 3 wherein the N.S.A.I.D. in the composition administered is Diclofenac Sodium.

6. A method for the immediate relief of pain associated with aphthous ulcers comprising administering an effective dosage amount of a composition comprising a non-steroidal anti-inflammatory drug (N.S.A.I.D.) and a form of hyaluronic acid selected from the group consisting of hyaluronic acid and pharmaceutically acceptable salts thereof, wherein the form of hyaluronic acid has a molecular weight less than 750,000 daltons and greater than 150,000 daltons.

7. The method of claim 6 wherein the form of hyaluronic acid is sodium hyaluronate.

8. The method of claim 6 or 7 wherein the effective dosage amount of the composition comprises an equivalent dosage amount of at least 18–25 mg. of a composition containing 2½% by weight of the form of hyaluronic acid and 3% by weight of the N.S.A.I.D.

9. The method of claim 8 wherein the N.S.A.I.D. is Diclofenac Sodium.

10. A method for the immediate relief of pain associated with aphthous ulcers, the method comprising applying a dosage amount of a pharmaceutical composition to the aphthous ulcer, said composition comprising a form of hyaluronic acid selected from hyaluronic acid and pharmaceutically acceptable salts thereof, and a non-steroidal anti-inflammatory drug (NSAID), said amount of hyaluronic acid is at least about 0.375–0.625 mg. and said N.S.A.I.D. is at least about 0.45–0.75 mg. of N.S.A.I.D. and wherein said form of hyaluronic acid has a molecular weight less than 750,000 daltons and greater than 150,000 daltons.

11. The method of claim 10 wherein the form of hyaluronic acid is sodium hyaluronate and said NSAID is diclofenac sodium.

12. A dosage amount of a pharmaceutical composition comprising:

(i) an effective non-toxic dosage amount of a form of hyaluronic acid selected from hyaluronic acid and a pharmaceutically acceptable salt thereof, each having a molecular weight less than 750,000 daltons and greater than 150,000 daltons; and combinations thereof in the order of about 0.375–0.625 mg. per dosage application or more and (ii) an effective non-toxic dosage amount of a non-steroidal anti-inflammatory drug (N.S.A.I.D.) in an amount effective to provide immediate relief of pain associated with aphthous ulcers in each dosage amount of said N.S.A.I.D. equivalent to at least about 0.45–0.75 mg. or more of Diclofenac sodium.

13. The method of claim 1 wherein the trauma is aphthous ulcers.

* * * * *